United States Patent
Komoschinski et al.

(10) Patent No.: US 6,355,827 B1
(45) Date of Patent: Mar. 12, 2002

(54) PROCESS FOR PREPARING 2-CYANOINDAN-1-ONES

(75) Inventors: Joachim Komoschinski, Köln; Helmut Fiege, Leverkusen; Guido Steffan, Odenthal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/485,957

(22) PCT Filed: Aug. 13, 1998

(86) PCT No.: PCT/EP98/05142

§ 371 Date: Feb. 18, 2000

§ 102(e) Date: Feb. 18, 2000

(87) PCT Pub. No.: WO99/10315

PCT Pub. Date: Mar. 4, 1999

(30) Foreign Application Priority Data

Aug. 25, 1997 (DE) ......................................... 197 36 921

(51) Int. Cl.$^7$ ............................................ C07C 253/14
(52) U.S. Cl. ..................................................... 558/342
(58) Field of Search .......................................... 558/342

(56) References Cited

U.S. PATENT DOCUMENTS 2,715,137 A * 8/1955 Copelin .................... 260/465.8
4,705,782 A * 11/1987 Logan et al. ................ 514/150

FOREIGN PATENT DOCUMENTS

WO  95/29171  11/1995
WO  96/20151  7/1996

OTHER PUBLICATIONS

Journal of the American Chemical Society, vol. 67, Jul.–Dec. 1945, pp. 1745–1754 (see page 1751) Johnson et al, A Plan for distinguishing between Some Five–and Six–membered Ring Ketones.

* cited by examiner

*Primary Examiner*—Floyd D. Higel
*Assistant Examiner*—Ebenezer Sackey
(74) *Attorney, Agent, or Firm*—Joseph C. Gil; Diderico van Eyl

(57) ABSTRACT

In a particularly advantageous process for producing 2-cyanoindan-1-ones from 2-halogenated indan-1-ones by reaction with a cyanide salt, the cyanide salt is dissolved in a dipolar aprotic solvent or in a water-miscible ether and 2-halogenated indan-1-one is metered into this solution.

10 Claims, No Drawings

PROCESS FOR PREPARING 2-CYANOINDAN-1-ONES

This application is a 371 of PCT/EP/98/05142 filed Aug. 13, 1998.

BACKGROUND OF THE INVENTION

The present invention relates to an improved process for preparing 2-cyanoindan-1-ones from corresponding 2-halogenoindan-1-ones by reaction with cyanide salts.

2-cyanoindan-1-ones are precursors for active compounds as described, for example in WO 96/20151 and WO 95/29171.

It is already known that 2-cyanoindan-1-one and 2-cyano-5-methoxyindan-1-one can be obtained by reacting the corresponding 2-bromoindan-1-ones with the aid of cyanide salts. Thus, J. Am. Chem. Soc. 66, 220 (1944) and 67, 1751 (1945) describe the preparation of these cyanoindan-1-ones by admixing 2-bromoindan-1-one and 2-bromo-5-methoxyindan-1-one, respectively, sodium cyanide or potassium cyanide, ethanol and water, and boiling this mixture at reflux. The yields obtained here are at best 52 and 73%, respectively. Moreover, a 10-fold molar excess of cyanide is employed, involving considerable work-hygienic expense during work-up.

DESCRIPTION OF THE INVENTION

We have now found a process for preparing 2-cyanoindan-1-ones of the formula

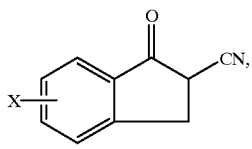

(I)

in which
X represents hydrogen, halogen, methyl, trifluoromethyl or methoxy,
from 2-halogenoindan-1-ones of the formula

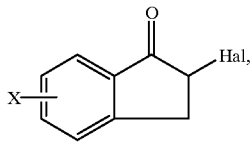

(II)

in which
X is as defined under formula (I) and
Hal represents chlorine or bromine,
by reaction with a cyanide salt, characterized in that the cyanide salt is initially charged dissolved in a dipolar aprotic solvent or in a water-miscible ether and the 2-halogenoindan-1-one of the formula (II) is metered into this solution.

Halogen is preferably fluorine, chlorine or bromine.

In the formulae (I) and (II), X preferably represents chlorine, in particular chlorine in the 5 or 6 position. Hal in formula (II) preferably represents chlorine.

Suitable cyanide salts are, for example, alkali metal cyanides and tetraalkylammonium cyanides. Examples include sodium cyanide, potassium cyanide, lithium cyanide, rubidium cyanide, tetraethylammonium cyanide and tetrabutylammonium cyanide. The cyanide salt in question can be employed, for example, in an amount of from 1.5 to 6 mol, based on 1 mole of the compound of the formula (II). This amount is preferably from 1.6 to 5 mol, in particular from 1.8 to 3 mol.

Suitable dipolar aprotic solvents are, for example, N-methylpyrrolidone, dimethylformamide, dimethylacetamide, dimethyl sulfoxide, hexamethylphosphoric triamide, sulfolane and acetonitrile, and suitable water-miscible ethers are, for example, tetrahydrofuran and diglycol dimethyl ether. Preference is given to dimethylformamide, dimethylacetamide, N-methylpyrrolidone and dimethyl sulfoxide.

Based on 1 mole of cyanide salt, for example from 200 to 2500 ml of dipolar aprotic solvent or water-miscible ether can be,employed. This amount is preferably from 300 to 1500 ml.

The 2-halogenoindan-1-one of the formula (II) is preferably metered in such that it is added in the dissolved form and a little at a time to the cyanide salt solution which has been initially charged. Suitable solvents for the 2-halogenoindan-1-one are likewise dipolar aprotic solvents and water-miscible ethers, as described in more detail above. Preference is given to using the same solvent for dissolving the cyanide salt and for preparing the solution of the 2-halogenoindan-1-one.

Preference is furthermore given to employing the 2-halogenoindan-1-one as a 10 to 30% by weight strength, in particular as a 15 to 25% by weight strength, solution.

The cyanide salt solution and/or the 2-halogenoindan-1-one solution may, if appropriate, contain water. For example, based on the solvent, up to 30% by weight of water may be present. This amount is preferably from 2 to 10% by weight.

The process according to the invention can, if appropriate, be carried out with addition of acids to control the pH. At a high pH, there is the risk that, in addition to the exchange of halogen for cyano, an elimination of hydrogen halide takes place. Accordingly, it is advantageous to control the pH, if appropriate, by addition of a strong acid, and to keep it, for example, in the range from 4 to 11, preferably from 5 to 10. Excessive acidification should be avoided, since this leads to the formation of hydrogen cyanide from the cyanide salt.

The acid can be added to the reaction mixture for example as such, but also, for example, together with the 2-halogenoindan-1-one or its solution.

Suitable acids are, in particular, aqueous acids of medium to high strength, such as aqueous hydrochloric acid, hydrobromic acid, sulfuric acid, phosphoric acid, formic acid and acetic acid.

The process according to the invention can be carried out, for example, at temperatures in the range from 10 to 70° C. Preference is given to temperatures in the range from 20 to 60° C.

The reaction mixture that is present after the process according to the invention has been carried out can be worked up, for example, in that it is cooled, any solvents present are stripped off under reduced pressure, the crystal slurry that remains is mixed with water and acidified slightly and the solid which is then present is filtered off and washed with water. If appropriate, the resulting 2-cyanoindan-1-one of the formula (I) can be purified further, for example by recrystallization from an organic solvent.

Using the process according to the invention, it is possible to obtain 2-cyanoindan-1-ones of the formula (I) in surprisingly high yields of 95% and more, employing considerably lower amounts of cyanide than in the prior-art process.

EXAMPLES

Example 1

10.4 g of sodium cyanide were dissolved in a mixture of 100 ml of dimethylformamide and 6 ml of water and initially charged. This solution was heated with stirring to 50° C., and 20.4 g of 2,5-dichloroindan-1-one, dissolved in 100 ml of dimethylformamide, were then added dropwise over a period of 60 minutes. After the addition had ended, stirring was continued at 50° C. for 1 hour. The mixture was then allowed to cool to room temperature and the solvent was stripped off using a rotary evaporator. The resulting crystal slurry was mixed with 200 ml of water and acidified to pH 4.5 using 10% by weight strength aqueous hydrochloric acid. The precipitated solid was filtered off with suction, washed with water, recrystallized from toluene and dried in a vacuum drying cabinet. This gave 18.5 g of 2-cyano-5-chloroindan-1-one (yield: 97% of theory).

Example 2

Example 1 was repeated using 2,6-dichloroindan-1-one instead of 2,5-dichloroindan-1-one. This gave 2-cyano-6-chloroindan-1-one in a yield of 95.5% of theory.

Example 3

(For Comparison)

A solution of 4.2 g of 2,5-dichloroindan-1-one in 140 ml of methanol was admixed first with 9.6 g of sodium cyanide and then with sufficient water to give a homogeneous solution. This mixture was boiled under reflux on a water bath for 45 minutes and then cooled to room temperature. After dilution with more water, the mixture was extracted twice with diethyl ether. The aqueous solution that remained was acidified with cold hydrochloric acid. The crude 2-cyano-5-chloroindan-1-one was separated off and taken up in chloroform. This solution was then clarified using Norit and subsequently extracted with small portions of a 5% by weight strength aqueous sodium hydroxide solution until no more precipitation was observed on acidification of a sample. Acidification of the combined aqueous phases gave 2.85 g of product which, after recrystallization from toluene, afforded 2.7 g of 2-cyano-5-chloroindan-1-one (yield: 70% of theory).

Although the present invention has been described in detail with reference to certain preferred versions thereof, other variations are possible. Therefore, the spirit and scope of the appended claims should not be limited to the description of the versions contained therein.

What is claimed is:

1. Process for preparing a 2-cyaniondan-1-one of the formula (I)

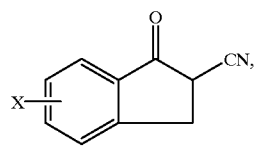

wherein X represents hydrogen, halogen, methyl, trifluoromethyl or methoxy, comprising reacting A) a 2-halogenoindan-1-one of the formula (II)

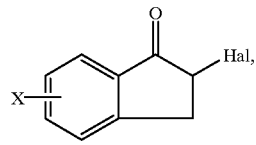

wherein
X is as defined under formula (I) and
Hal represents chlorine or bromine, with B) a cyanide salt, wherein the cyanide salt is initially charged and dissolved in a dipolar aprotic solvent or in a water-miscible ether and the 2-halogenoindan-1-one of the formula (II) is metered into this solution.

2. Process according to claim 1, wherein in the formulae X and Hal each represent chlorine.

3. Process according to claim 1, wherein from 1.6 to 6 mol of cyanide salt are employed per mole of a compound of the formula (II).

4. Process according to claim 1, wherein the dipolar aprotic solvent or water-miscible ether used is selected from the group consisting of N-methylpyrrolidone, dimethylformamide, dimethylacetamide, dimethyl sulfoxide, hexamethylphosphoric triamide, sulfolane, acetonitrile, tetrahydrofuran and diglycol dimethyl ether.

5. Process according to claim 1, wherein the 2-halogenoindan-1-one of the formula (II) is added in the dissolved form and a little at a time to the cyanide salt solution which has been initially charged.

6. Process according to claim 1, wherein the 2-halogenoindan-1-one of the formula (II) is employed as a 10 to 30% by weight strength solution.

7. Process according to claim 1, wherein based on the solvent, up to 30% by weight of water are present.

8. Process according to claim 1, wherein the pH is kept in the range from 4 to 11 by addition of a strong acid.

9. Process according to claim 1, wherein the process is carried out at from 10 to 70° C.

10. Process according to claim 1, wherein the reaction mixture which is present after the reaction is worked up in that it is cooled, and any solvents present are stripped off under reduced pressure, and the crystal slurry that remains is mixed with water and acidified slightly and the solid is filtered off and washed with water.

* * * * *